United States Patent [19]

Arhancet

[11] Patent Number: 5,489,718
[45] Date of Patent: Feb. 6, 1996

[54] COMPOSITIONS AND METHODS FOR INHIBITING VINYL AROMATIC MONOMER POLYMERIZATION

[75] Inventor: Graciela B. Arhancet, Katy, Tex.

[73] Assignee: Betz Laboratories, Inc., Trevose, Pa.

[21] Appl. No.: 392,693

[22] Filed: Feb. 23, 1995

Related U.S. Application Data

[62] Division of Ser. No. 269,308, Jun. 3, 1994, Pat. No. 5,426,257.

[51] Int. Cl.⁶ ...................................................... C07C 7/20
[52] U.S. Cl. .................. 585/5; 585/4; 585/3; 208/48 AA
[58] Field of Search .................... 585/5, 3, 4; 208/48 AA

[56] References Cited

U.S. PATENT DOCUMENTS

| | | | |
|---|---|---|---|
| 4,061,545 | 12/1977 | Watson et al. | 203/9 |
| 4,466,905 | 8/1984 | Butler et al. | 252/403 |
| 4,720,566 | 1/1988 | Martin | 558/306 |
| 4,774,374 | 9/1988 | Abruscato et al. | 585/24 |
| 5,169,410 | 12/1992 | Wright | 44/415 |
| 5,266,726 | 11/1993 | Pastor et al. | 564/268 |
| 5,396,004 | 3/1995 | Arhancet et al. | 585/5 |
| 5,416,258 | 5/1995 | Arhancet et al. | 585/3 |
| 5,426,257 | 6/1995 | Arhancet | 585/5 |

*Primary Examiner*—Asok Pal
*Assistant Examiner*—Bekir L. Yildirim
*Attorney, Agent, or Firm*—Alexander D. Ricci; Philip H. Von Neida

[57] ABSTRACT

Compositions and methods for inhibiting polymerization of vinyl aromatic monomers in oxygen-free processing systems are disclosed. The compositions comprise an oxime compound and a hydroxylamine compound and, alternatively, an oxime compound, a hydroxylamine compound and a phenylenediamine compound. The methods comprise adding either of the compositions to the vinyl aromatic monomer in an amount ranging from 1 to about 10,000 parts per million parts monomer.

14 Claims, No Drawings

COMPOSITIONS AND METHODS FOR INHIBITING VINYL AROMATIC MONOMER POLYMERIZATION

This is a divisional of application Ser. No. 09/269,308 filed Jun. 3, 1994, now U.S. Pat. No. 5,426,257.

FIELD OF THE INVENTION

This invention relates to compositions and methods for inhibiting the unwanted polymerization of vinyl aromatic monomers during processing.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, although virtually excluded in styrene distillation, will also promote polymerization of the monomer.

This polymerization results not only in loss of desired monomer end-product, but also in the loss of production efficiency caused by polymer formation and/or agglomeration of polymer on process equipment. Thermal polymerization of styrene monomer results in the formation of normal (i.e., linear) polymer. This resulting polystyrene polymer is characterized by its glassy and transparent appearance and its solubility in the styrene monomer and many organic solvents.

SUMMARY OF THE INVENTION

The present invention provides for methods for inhibiting the polymerization of vinyl aromatic monomers, such as styrene, and compositions comprising synergistic combinations of actives. The present inventor has discovered that oxime compounds in combination with a hydroxylamine compound and in combination with a hydroxylamine compound and a phenylenediamine compound, will effectively inhibit the unwanted polymerization of vinyl aromatic monomers during their processing.

DESCRIPTION OF THE RELATED ART

The compounds generally used commercially to prevent polymerization of vinyl aromatic monomers are of the dinitrophenolic type. For example, U.S. Pat. No. 4,105,506, Watson, et al., teaches the use of 2,6-dinitro-p-cresol as polymerization inhibitor of vinyl aromatic compounds. U.S. Pat. No. 4,466,905, Butler et al., teaches that 2,6-dinitro-p-cresol and p-phenylenediamines will inhibit polymerization in the distillation column if oxygen is present. U.S. Pat. No. 4,774,374, Abruscato et al., teaches compositions and processes for inhibiting the polymerization of a vinyl aromatic compound employing an oxygenated species formed by the reaction of oxygen and a N-aryl-N'-alkyl-p-phenylenediamine. U.S. Pat. No. 4,720,566, Martin, teaches methods and compositions for inhibiting polymerization of acrylonitrile in the quench tower, no oxygen excluded, using a hydroxylamine compound and a phenyl-p-phenylenediamine compound.

A variety of inhibitor compositions have been employed in styrene and other vinyl aromatic monomers to inhibit undesirable polymerization. Amongst others, agents that have been used include sulfur, p-benzoquinone, phenylenediamines, tert-butyl pyrocatechol, phenothiazine, hydroxylamines, nitrocompounds, and hindered phenols. However, many of these compounds present disadvantages such as high toxicity, instability and explosion hazard under elevated temperature, or insufficient efficacy under processing conditions (i.e., inhibitor requires oxygen to be effective). The present inventor has discovered a novel method for inhibiting vinyl aromatic monomer polymerization that avoids these problems associated with known inhibitors.

DETAILED DESCRIPTION OF THE INVENTION

The present invention relates to compositions and methods for inhibiting the polymerization of vinyl aromatic monomers in an oxygen-free vinyl aromatic monomer processing system comprising adding to the monomers a combination of an oxime compound and a hydroxylamine compound, or in an alternative embodiment, a combination of an oxime compound, a hydroxylamine compound, and a phenylenediamine compound.

The compositions of the present invention prove effective at inhibiting the polymerization of vinyl aromatic monomers under monomer processing conditions. These processing conditions include but are not limited to the purification and distillation processes of vinyl aromatic monomers.

The vinyl aromatic monomers that can be treated by the present invention include but are not limited to styrene, bromostyrene, divinylbenzene and α-methylstyrene. The compositions of the present invention are particularly efficacious at inhibiting polymerization of styrene monomer.

The phrase "oxygen-free processing conditions" is meant to define the substantially oxygen free conditions under which vinyl aromatic monomers, particularly styrene, are processed. These conditions, exemplified by distillation and purification processes, generally have less than 2 parts per million oxygen present and preferably less than 1 part per million oxygen per parts styrene.

The oxime compounds generally have the formula

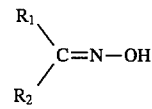

wherein $R_1$ and $R_2$ are the same or different and are hydrogen, alkyl, aryl, alkaryl, aralkyl, alkylhydroxyaryl or arylhydroxyalkyl groups having three to about twenty carbon atoms. The preferred oxime compounds are salicylaldoxime, 5-dodecyl-salicyladoxime and alkyl acetophenone oxime.

The hydroxylamine compounds useful in this invention generally have the formula

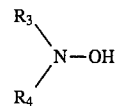

wherein R and R are the same or different and are hydrogen, alkyl, aryl, alkaryl, aralkyl, or hydroxyalkyl groups and preferably have three to about twenty carbon atoms. The preferred hydroxylamine compound is bis-(hydroxypropyl)hydroxylamine (HPHA).

The phenylenediamine compounds useful in this invention generally have the formula

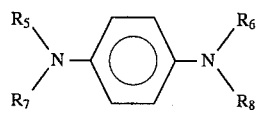

wherein $R_5$, $R_6$, $R_7$ and $R_8$ are the same or different and are hydrogen, alkyl, aryl, alkaryl or aralkyl groups having one to about twenty carbon atoms. The preferred phenylenediamine compound are N, N'-di-sec-butyl-p-phenylenediamine and N-phenyl-N'-(1,4-dimethylpentyl)-p-phenylenediamine.

The compositions of the present invention prove effective at inhibiting the polymerization of vinyl aromatic monomers during oxygen-free processing. The inventive compositions provide enhanced activity over each separate component in styrene monomer undergoing distillation and purification processes at elevated temperatures. Styrene is typically processed at temperatures between 95° and 125° C. The compositions of the present invention prove particular efficacy in higher temperature (>110° C.) styrene monomer processing systems.

The total amount of oxime compound and hydroxylamine compound (composition I) and oxime compound, hydroxylamine compound and phenylenediamine compound (composition II) used in the methods of the present invention is that amount which is sufficient to inhibit polymerization and will vary according to the conditions under which the vinyl aromatic monomer is being processed and exposed to high temperatures. At higher temperature and higher monomer contamination, larger amounts of polymerization inhibiting composition are generally required.

Preferably, the total amount of composition I or composition II added to the vinyl aromatic monomer ranges from 1 to about 10,000 parts per million parts monomer. More preferably, the treatment range is from about 5 parts to about 500 parts of the composition per million parts monomer.

The weight ratio of oxime compound to hydroxylamine compound in composition I ranges from about 9:1 to 1:9 with 2:1 to 9:1 preferred. The weight ratio of oxime to hydroxylamine to phenylenediamine in composition II ranges from about 1–9 to 1–9 to 1–9.

The compositions of the present invention can be added to the vinyl aromatic monomer by any conventional method, either as individual ingredients or as a combination of ingredients. It is preferred for both composition I and II that they are added as a single treatment composition.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer may be employed.

Accordingly, it is possible therefore to produce a more effective vinyl aromatic monomer polymerization inhibition treatment than is obtainable by the use of any one ingredient alone when measured at comparable treatment levels. This enhanced activity, as evidenced by both composition I and composition II, allows for the concentration of each of these ingredients to be lowered and the total quantity of polymerization inhibitor required, particularly at higher processing temperatures, may be reduced.

The preferred inventive embodiment of composition I employs bis-(hydroxypropyl)hydroxylamine with salicylaldoxime. The preferred inventive embodiment of composition II employs bis-(hydroxypropyl)hydroxylamine N,N'-di-sec-butyl-p-phenylenediamine with salicylaldoxime.

This invention will now be further described with reference to a number of specific examples which are to be regarded solely as illustrative, and not as restricting the scope of the invention.

EXAMPLES

In order to evaluate the improved polymerization inhibition of the inventive compositions and to demonstrate the enhanced activity of each composition, styrene polymerization testing was performed.

Uninhibited styrene (5 mL) was placed in a test tube and the appropriate amount of treatment was added. The tube was capped with a septum and argon was bubbled through the liquid at 15 mL/min for 3 minutes. Then, the tubes were placed in an oil bath heated to 120° C. for 2 hours. The amount of polystyrene formed was determined by methanol precipitation. Results of this testing are summarized in Table I.

TABLE I

| Treatment | Dose (ppm) | Percent Polymer |
|---|---|---|
| Styrene polymerization test Uninhibited Styrene 120° C. | | |
| SA | 600 | 19.40 |
| DDSA | 600 | 19.40 |
| AAO | 600 | 18.68 |
| HPHA | 600 | 8.56 |
| HPHA/SA | 300/300 | 0.93 |
| HPHA/SA | 150/450 | 7.27 |
| HPHA/SA | 450/150 | 0.67 |
| HPHA/SA | 200/400 | 4.40 |
| HPHA/SA | 400/200 | 0.89 |
| HPHA/SA | 100/500 | 10.22 |
| HPHA/SA | 500/100 | 1.44 |
| HPHA/DDSA | 300/300 | 1.60 |
| HPHA/DDSA | 450/150 | 0.70 |
| HPHA/AAO | 300/300 | 4.84 |
| HPHA/AAO | 450/150 | 5.01 |

SA is salicylaldoxime
DDSA is 5-dodecylsalicylaldoxime, available from Henkel as Aloxime 800
AAO is alkyl acetophenone oxime, available from Henkel as Aloxime 840
HPHA is bis-(hydroxypropyl)hydroxylamine The results of this testing indicate that composition I, oxime compound and hydroxylamine compound, provides enhanced activity over that of either ingredient alone at inhibiting the polymerization of styrene. Hydroxylamine compounds are known polymerization inhibitors for styrene, yet the polymerization inhibition of the combination exceeded that of a hydroxylamine compound employed alone.

Further testing was performed utilizing the procedure described for Table I for composition II. These results are reported in Table II.

TABLE II

| Treatment | Dose (ppm) | Percent Polymer |
|---|---|---|
| Styrene polymerization test Uninhibited Styrene 120° C. | | |
| PD/HPHA | 200/300 | 4.10 |
| SA | 600 | 19.40 |
| DDSA | 600 | 19.40 |
| AAO | 600 | 18.68 |
| PDA/HPHA/SA | 200/300/100 | 0.24 |
| PDA/HPHA/SA | 200/300/50 | 0.51 |

TABLE II-continued

Styrene polymerization test
Uninhibited Styrene
120° C.

| Treatment | Dose (ppm) | Percent Polymer |
|---|---|---|
| PDA/HPHA/SA | 200/300/25 | 1.30 |
| PDA/HPHA/DDSA | 200/300/100 | 0.92 |
| PDA/HPHA/AAO | 200/300/100 | 1.76 |

PDA is N,N'-di-sec-butyl-p-phenylenediamine
HPHA is bis-(hydroxypropyl)hydroxylamine
SA is salicylaldoxime
DDSA is 5-dodecylsalicylaldoxime, available from Henkel as Aloxime 800.
AAO is alkyl acetophenone oxime, available from Henkel as Aloxime 840.

The results of this testing indicate that composition II of the present invention, oxime compound, hydroxylamine compound and phenylenediamine compound, provides enhanced activity over that of hydroxylamine/phenylenediamine combination or the use of oxime compounds singly as polymerization inhibitors. These results, as in Table I, show that the inventive compositions provide enhanced activity at inhibiting polymerization over that of the individual components at elevated styrene processing temperatures. Further, the addition of an oxime compound to a known polymerization inhibitor, hydroxylamine compound and phenylenediamine, resulted in better inhibition of polymerization than the known inhibitor pair.

Uninhibited styrene (100 mL) was placed in a 250-mL three-necked flask fitted with a bubbler, a septa, and a condenser. The appropriate treatment was added and argon was bubbled through the solution at 10 mL/min for 10 minutes. Then, while argon sparging continued, the flask was immersed in an oil bath heated at 120° C. Samples (5.0 mL) were taken every 30 minutes and the amount of polymer formed was determined by methanol precipitation. The results of this testing for compositions I and II are presented below in Tables III and IV.

TABLE III

Styrene polymerization test under argon
120° C.
Treatment: bis-hydroxypropylhydroxylamine/salicylaldoxime
300 ppm of each

| Time (min) | % Polymer |
|---|---|
| 30 | 0.04 |
| 60 | 0.10 |
| 90 | 0.19 |
| 120 | 0.29 |
| 150 | 0.54 |
| 180 | 3.30 |

TABLE IV

Styrene polymerization test under argon
120° C.
600 ppm total treatments, 1:2:1 ratios

| Treatment SA/HPHA/I-3 | | Treatment SA/HPHA/PDA | |
|---|---|---|---|
| Time (min) | % Polymer | Time (min) | % Polymer |
| 30 | 0.01 | 30 | 0.01 |
| 60 | 0.03 | 60 | 0.02 |
| 90 | 0.05 | 90 | 0.05 |

TABLE IV-continued

Styrene polymerization test under argon
120° C.
600 ppm total treatments, 1:2:1 ratios

| Treatment SA/HPHA/I-3 | | Treatment SA/HPHA/PDA | |
|---|---|---|---|
| Time (min) | % Polymer | Time (min) | % Polymer |
| 120 | 0.10 | 120 | 0.10 |
| 150 | 0.35 | 150 | 0.17 |
| 180 | 0.76 | 180 | 0.28 |

SA is salicylaldoxime
HPHA is bis-(hydroxypropyl)hydroxylamine
I-3 is N-phenyl-N'-(1,4-dimethylpentyl)-p-phenylenediamine
PDA is N,N'-di-sec-butyl-p-phenylenediamine These results indicate that the inventive compositions, I and II, provide enhanced activity at inhibiting styrene polymerization at elevated process conditions and in oxygen-free processing environments.

While this invention has been described with particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A vinyl aromatic monomer polymerization inhibiting composition comprising an oxime compound and a hydroxylamine compound.

2. The composition as claimed in claim 1 wherein said oxime compound has the formula

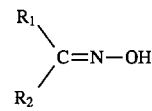

wherein $R_1$ and $R_2$ are the same or different and are hydrogen, alkyl, aryl, alkaryl, aralkyl, alkylhydroxyaryl or arylhydroxyalkyl groups and have three to about twenty carbon atoms.

3. The composition as claimed in claim 1 wherein said oxime compound is selected from the group consisting of salicylaldoxime, 5-dodecylsalicylaldoxime and alkyl acetophenone oxime.

4. The composition as claimed in claim 1 wherein said hydroxylamine compound has the formula

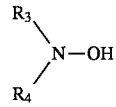

wherein $R_3$ and $R_4$ are the same or different and are hydrogen, alkyl, aryl, alkaryl, aralkyl, or hydroxyalkyl groups and have three to about twenty carbon atoms.

5. The composition as claimed in claim 1 wherein said hydroxylamine compound is bis-(hydroxypropyl)hydroxylamine.

6. The composition as claimed in claim 1 wherein said oxime compound and said hydroxylamine compound are in a weight ratio from about 9:1 to 1:9.

7. A vinyl aromatic monomer polymerization inhibiting composition comprising an oxime compound, a hydroxylamine compound and a phenylenediamine compound.

8. The composition as claimed in claim 7 wherein said oxime compound has the formula

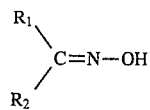

wherein $R_1$ and $R_2$ are the same or different and are hydrogen, alkyl, aryl, alkaryl, aralkyl, alkylhydroxyaryl or arylhydroxyalkyl groups and have three to about twenty carbon atoms.

9. The composition as claimed in claim 7 wherein said oxime compound is selected from the group consisting of salicylaldoxime, 5-dodecylsalicylaldoxime and alkyl acetopheneone oxime.

10. The composition as claimed in claim 7 wherein said hydroxylamine compound

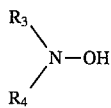

wherein $R_3$ and $R_4$ are the same or different and are hydrogen, alkyl, aryl, alkaryl, aralkyl, or hydroxyalkyl groups and have three to about twenty carbon atoms.

11. The composition as claimed in claim 7 wherein said hydroxylamine compound is bis-(hydroxypropyl)hydroxylamine.

12. The composition as claimed in claim 7 wherein said phenylenediamine compound has the formula

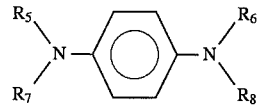

wherein $R_5$, $R_6$, $R_7$, and $R_8$ are the same or different and are hydrogen, alkyl, aryl, alkaryl, or aralkyl groups having one to about twenty carbon atoms.

13. The composition as claimed in claim 7 wherein said phenylenediamine compound is selected from the group consisting of N,N'-di-sec-butyl-p-phenylenediamine and N-phenyl-N'-(1,4-dimethylpenyl)-p-phenylenediamine.

14. The composition as claimed in claim 7 wherein the weight ratio of oxime compound to hydroxylamine compound to phenylenediamine compound is about 1–9 to 1–9 to 1–9.

* * * * *